US012629456B2

(12) United States Patent
Schurmann-Kaufeld et al.

(10) Patent No.: US 12,629,456 B2
(45) Date of Patent: May 19, 2026

(54) STENT WITH IMMEDIATELY REMOVEABLE COATING

(71) Applicant: InnoRa GmbH, Berlin (DE)

(72) Inventors: Sebastian Schurmann-Kaufeld, Berlin (DE); Nadia Brunacci, Berlin (DE)

(73) Assignee: InnoRa GmbH, Berlin (DE)

( * ) Notice: Subject to any disclaimer, the term of this patent is extended or adjusted under 35 U.S.C. 154(b) by 952 days.

(21) Appl. No.: 17/617,752

(22) PCT Filed: Jun. 18, 2020

(86) PCT No.: PCT/EP2020/066852
§ 371 (c)(1),
(2) Date: Dec. 9, 2021

(87) PCT Pub. No.: WO2020/254454
PCT Pub. Date: Dec. 24, 2020

(65) Prior Publication Data
US 2022/0241467 A1      Aug. 4, 2022

(30) Foreign Application Priority Data
Jun. 21, 2019    (DE) ..................... 10 2019 116 791.4

(51) Int. Cl.
| | |
|---|---|
| *A61F 2/958* | (2013.01) |
| *A61K 31/337* | (2006.01) |
| *A61L 27/28* | (2006.01) |
| *A61L 27/54* | (2006.01) |
| *A61L 29/08* | (2006.01) |
| *A61L 29/16* | (2006.01) |

(52) U.S. Cl.
CPC .............. *A61L 27/54* (2013.01); *A61F 2/958* (2013.01); *A61K 31/337* (2013.01); *A61L 27/28* (2013.01); *A61L 29/08* (2013.01); *A61L 29/16* (2013.01); *A61F 2240/001* (2013.01); *A61F 2250/0067* (2013.01); *A61L 2300/216* (2013.01); *A61L 2300/404* (2013.01); *A61L 2300/418* (2013.01); *A61L 2300/422* (2013.01); *A61L 2420/02* (2013.01)

(58) Field of Classification Search
CPC .......... A61L 27/54; A61L 27/28; A61L 29/08; A61L 29/16; A61L 2420/02; A61F 2/958; A61F 2/90; A61F 2/915; A61F 2250/0067; A61K 31/337
See application file for complete search history.

(56) References Cited

U.S. PATENT DOCUMENTS

2010/0055294 A1* 3/2010 Wang ..................... B05D 3/107
427/2.3

FOREIGN PATENT DOCUMENTS

| | | |
|---|---|---|
| DE | 10 2014 106 422 A1 | 11/2015 |
| WO | 2008/003298 A2 | 1/2008 |

(Continued)

OTHER PUBLICATIONS

International Search Report, mailed Aug. 19, 2020 in International Application No. PCT/EP2020/066852.

(Continued)

*Primary Examiner* — Brian A Dukert
(74) *Attorney, Agent, or Firm* — Wood, Phillips, Katz, Clark & Mortimer

(57) ABSTRACT

An implantable medical device which is coated with a rapidly releasable substance.

12 Claims, 2 Drawing Sheets

(56)                   References Cited

FOREIGN PATENT DOCUMENTS

| WO | 2008/086794 | A2 | 7/2008 |
| WO | 2010/024898 | A2 | 3/2010 |

OTHER PUBLICATIONS

International Preliminary Report on Patentability and Written Opinion of the International Searching Authority, Issued Dec. 21, 2021 in International Patent Application No. PCT/EP2020/066852.

* cited by examiner

STENT WITH IMMEDIATELY REMOVEABLE COATING

BACKGROUND OF THE INVENTION

Field of the Invention

The invention relates to an implantable medical device, preferably a stent for arteriosclerosis-conditioned vascular stenosis, as well as to a method for the production thereof.

Background Art

The combination of medicinal products with medical devices has been shown to be advantageous in many clinical applications. An important area is the prevention of unwanted vascular changes following mechanical interventions. In this regard, mechanically stable supports are inserted permanently or temporarily into the vascular lumen (known as stents or stent grafts) or the vascular wall is treated mechanically by means of a balloon of a balloon catheter and at the same time protected from unwanted changes by means of a medicinal product.

Stents are tubular entities which are usually introduced into the body with a small diameter, for example into blood vessels, bile ducts or other duct-shaped structures, occasionally also into tissues or structures which are solid to a greater or lesser extent. In a second step and only at the application site, they attain a larger diameter which guarantees a sufficiently large internal lumen (for example for unhindered blood flow). This step can be carried out by releasing the radially compressed stent consisting of an elastic material (for example nitinol) from a tube or catheter, or by active expansion by means of a balloon of a balloon catheter, inter alia, for stents produced from plastically deformable materials such as steel or cobalt-chrome alloys, or in fact other alloys. Constricted or blocked blood vessels, constricted ducts or the direct creation of passages in tissue are routine points of use for stents.

In each case, stents which have been available until now and which are coated with medicinal products or are uncoated, are permanent implants. Even the recently publicized and occasionally used biodegradable stents remain at the implantation site for weeks, months or years.

The implantation of stents is usually associated with the forced opening or re-opening of passages; this leads to substantial damage to the surrounding tissue. During healing, tissue proliferation or scarring occurs which lasts for months, which in turn can result in narrowing or closing up of the free passages created by the stent. This can sometimes be highly effectively prevented by coating the stents with slow-eluting substances which inhibit the excessive and sustained proliferation of tissue. It has been and remains the belief that only long-term elution of the substances from the stents guarantees a long-lasting effect (Gershlick A H. Treating atherosclerosis: local drug delivery from laboratory studies to clinical trials. Atherosclerosis 2002; 160:259-271. p 267: "Retention, which is very much the problem with non-stent drug delivery can be overcome if the agent can be attached to the stent but then be made to elute off slowly once the stent is deployed"; Iofina E, Langenberg R, Blindt R, Kühl H, Kelm M, Hoffmann R. Polymer-based paclitaxel-eluting stents are superior to nonpolymer-based paclitaxel-eluting stents in the treatment of de novo coronary lesions. Am J Cardiol. 2006; 98: 1022-1027 "Achieving the correct balance between rate of elution and degree of retention is clearly important" or Müller-Hülsbeck St. Eluvia™ peripheral stent system for the treatment of peripheral lesions above the knee. Expert Opin. Drug Deliv 2016; 13: 1639-1644: "The available preclinical and clinical data on treatment with Eluvia™ suggest that prolonged paclitaxel elution in the femoropopliteal arteries prevents restenosis and may reduce the need for reintervention.").

As permanent implants, stents constitute an ideal prerequisite for delayed long-term elution. However, stents are extremely delicate structures in order for them to be as non-invasive as possible and grow in as rapidly as possible following implantation and cause minimum local inflammation. The low masses and surface areas of the stents very substantially limits the dose of medicinal product which can be deposited on them. Highly effective, delayed-eluting medicinal products on stents for coronary arteries are practically routine. The first effective products for peripheral arteries have also been authorized and are already in use in that area.

Alternatively, in the last 15 years, balloon catheters coated with medicinal product have been developed, authorized and introduced into clinical practice in selected indications. Paclitaxel is the preferred medicinal product. Balloons of balloon catheters block the blood flow when inflated. Thus, in coronary arteries, in most cases they can only be inflated for a maximum of 1 minute; in leg arteries, inflation times of a few minutes are possible. In this brief period, the medicinal product has to be released as fully as possible from the balloon membrane and a sufficient proportion has to be transferred to the vascular wall.

For a vessel of identical diameter and identical length to be treated, coated balloons of balloon catheters contain far more medicinal product than coated stents. The higher dose of medicinal product on the balloons should be understood to be by way of compensation for the incomplete transfer from the balloon into the vessel wall or by way of compensation for the lack of a sustained flow of medicinal product from a permanent implant. Thus, very different principles were employed when coating stents and balloons with medicinal products (Table 1).

TABLE 1

| Coating of medical devices for opening passages or cavities or keeping them open in the body using medicinal products/(coronary) substances | | | | | |
|---|---|---|---|---|---|
| Medical product | Time in contact with tissue for treatment [time] | Medicinal product | Dose (example: stent/ balloon approx. 3 mm Ø, 20 mm long) | Surface area for receipt of medicinal products directed towards vessel wall [area] | Release of medicinal product [time] |
| Stent steel, cobalt-chrome) | permanent | Sirolimus paclitaxel | 100 µg | 38 mm$^2$ | days to months |
| Stent, bio-degradable | years | Sirolimus, everolimus, novolimus, biolimus | 150 µg | <100 mm$^2$ | approx. 80% in 4 weeks |
| Balloon | seconds to a few minutes | Paclitaxel sirolimus | 400-600 µg 250 µg | 190 mm$^2$ | seconds to a few minutes |

The delayed delivery of the substances from stents is achieved by means of diffusion. Diffusion occurs from water-insoluble polymers or from very special, highly adhesive, very slowly soluble or biodegradable coatings. The delay in delivery from stents is also promoted by the production of particularly low-solubility modifications to the medicinal products, for example by post-treatment of the coated stents (annealing).

Problems with the long-term sustained delivery of proliferation-inhibiting medicinal products are the formation of thrombotic blockages in the stent (stent thromboses) as well as degeneration of the arterial wall, which is detached from the stent and therefore prevents or delays ingrowth into the vessel wall and can lead to a change of position of the stent in the enlarging vessel lumen.

One approach to solving these problems is by way of self-expanding stents. Based on these, in recent years, medicinal product supports have been developed, such as those which are known from US 2017/0 196 717, for example. These are constructed to stretch the vessel wall and at the same time to introduce medicinal products deep into the vessel wall. In contrast to stents which had been used beforehand, stents of this type remain at the treatment site for only a few minutes and are subsequently completely removed from the vessel and the body of the patient. They consist of metal with a pronounced shape memory which, like the usual self-expanding stents, have approximately the desired diameter of the vessel lumen to be treated, but when they are to be introduced into the body, they are compressed to a very much smaller diameter. Problems with coating stents of this type are:

(a) uniformly coating an entity with a highly complicated structure, preferably in the expanded state, (b) application of the substance has to be carried out rapidly and as completely as possible, (c) but very good adhesion of the coating during compression of the stent is required, (d) adhesion during introduction through catheters which are filled with blood or other bodily fluids has to be guaranteed, (e) adhesion during deployment of the highly compressed stent from the catheter, as well as (f) reliable estimation of an effective dose.

SUMMARY OF THE INVENTION

Thus, one objective of the invention is to solve the aforementioned problem and in particular to provide a coating for implantable medical devices such as stents which, directly after contact with the tissue, for example the vessel wall, transfers an effective dose of medicinal product, and the coating is therefore "instantly elutable".

This objective is achieved by means of an implantable medical device with the features of the independent claim. Thus, in a first aspect, the invention concerns an implantable medical device, for example a stent for arteriosclerosis-conditioned vascular stenosis, comprising a main body with a substance and/or a mixture of substances applied to a surface of the main body. In accordance with the invention, the dose of the substance or of the substance mixture is at least 5 $\mu g/mm^2$ with respect to the coated surface.

Advantageously, this leads to rapid delivery of the substance. This guarantees that even with short residence times for the implantable medical device (hereinbelow also only medical devices; balloons of balloon catheters are not implanted and are not included here), a sufficient quantity of substance is transferred to the target site in order to counteract any renewed vascular constriction. In order to elute the substance, hereinbelow also termed the medicinal product, a time period of up to 20 min is preferred; even more rapid transfer rates such as 15 min or 10 min or less are more preferred. An elution period of up to 5 min is particularly preferred. In the present case, a rapid delivery of the substance is obtained if at least 40%, preferably more than 45%, more preferably at least 60%, particularly preferably at least 65% of the substance originally disposed on the surface of the medical device, i.e. before contact with the human body, is delivered into the surrounding tissue over the aforementioned time period.

In other words, in the context of the invention, the term "rapid and complete release" should be understood to mean that 10 to 20 min after the implantable medical device has been fully introduced into the human body, on average no more than 20%, preferably no more than 30%, in particular no more than 40% remains on the surface of the medical device.

Surprisingly, it has been shown that in contrast to the prevailing opinion, a rapid delivery of the substance in implantable or implanted medical devices, in particular stents, can effectively prevent restenosis. This was somewhat of a surprise considering that, in order to effectively prevent a restenosis, it has to be ensured that an effective dose of substance which is as uniformly distributed as possible is present in the affected tissue. In the case of balloon catheters, this is ensured by applying the substance over a large uniform surface area onto the surrounding tissue as completely as possible. In the case of stents which have been in use until now, in contrast, a continuous delivery of a smaller dose is carried out over a longer period of time. In this regard, the substance diffuses from the delivery site into the surrounding tissue. In contrast to balloon catheters, the distribution is obtained over the residence time of the implant.

It has been shown that a rapid elution or delivery of the substance in the case of implantable medical devices, in particular stents, in the embodiment of the implantable medical device in accordance with the invention, namely in a concentration of substance of at least 5 $\mu g/mm^2$ of the surface area, effectively prevents a restenosis.

Particularly advantageously, the substance or the substance mixture is present on the medical device in a non-bound form, i.e. not as a compound with substances which inhibit the delivery of the substance or substances. In other words, in addition to the restenosis-inhibiting substance, the coating on the surface of the medical device has no polymers or other compounds which substantially reduce the rate of delivery of the substance. This accelerates the delivery of the substance compared with previously known stents. As a consequence, deposits of substance are formed at the contact points of the surface of the medical device and tissue or in the tissue. The larger these deposits are, the more medicinal product will be transferred to the tissue over a short period.

In a preferred embodiment of the invention, on the coated surface of the main body, i.e. in particular on the surface of the medical device or stent which faces away from the vessel lumen when in its intended use, in addition to the substance, pharmaceutically routine additives and auxiliary substances are disposed. This should be understood to mean that expressly no compounds which inhibit the delivery of the substance, such as polymers, for example, are present. Additives of this type are, for example, suitable for improving the adhesion, delivery and stability of the substance or substance mixture or of the substance or the substance mixture-containing layer on the surface of the medical device prior to its implantation, for example in a blood vessel. In other words, pharmacologically harmless or mostly harmless auxiliary substances may be added to the substances. Suitable substances are auxiliary substances for improving adhesion prior to the intentional delivery of the substances, for accelerating the delivery of the substances, auxiliary substances which contribute to improving their chemical stability, which adjust the pH of the coating solutions, or which influence the structure of the layer, for example its flexibility, glide properties and solubility in water. Such auxiliary substances are known in the pharmaceuticals field and are routinely used as a mixture with medicinal products, even for coating balloon catheters; hydrophilic auxiliary substances such as iodized X-ray contrast agents, urea or in fact lipophilic antioxidants such as butylhydroxytoluene (BHT), resveratrol, nordihydroguajaretic acid (NDGA) and propyl gallate are well established for use on coated balloon catheters. A further preferred auxiliary substance is dexpanthenol, which combines the aforementioned properties with promotion of healing of the vessel wall. Solid flow agents such as magnesium stearate or other fatty acid salts are also preferred. Flow agents can be added to the coating or be applied afterwards to the coated medical device; to act effectively, it lies on the surface thereof.

Preferably, the main body comprises a metal, a synthetic material, a natural product or a combination of these materials, or is prepared therefrom. Particularly preferably, the main body consists, at least in areas, of steel, cobalt-chrome or nitinol, which is a nickel-titanium alloy.

The main bodies may be plastically deformable or elastically deformable. Alternatively or in addition, the main body is deformable by means of a specific arrangement of protrusions and cavities.

Advantageously, the medical device in accordance with the invention is only implanted temporarily, i.e. remains in the active position for only a predetermined period. Preferably, the time period is up to 30 min, in particular up to 15 min. Permanent implants, and therefore permanent changes to the vessel walls, are prevented.

In a preferred embodiment of the invention, furthermore, the medical device has a lumen and in the lumen of self-expandable stents, there is also a balloon for post-dilation. This enables the medical device, in particular the stent, to be expanded to a larger diameter at the specified site and/or during use without subsequently having to introduce a balloon and position it accurately later on. This increases the range of applications of the medical device and simplifies and speeds up its use.

The main body has an elongated shape which delimits the lumen. Spike-like elements which extend outwardly may be disposed on a surface of the main body which faces away from the lumen. When being used as intended, these elements act to introduce medical substances deep into the tissue. In the context of the invention, in this regard, the substance is disposed in intermediate regions between and/ or on these spike-like elements.

Introducing the substance into the tissue by means of the spike-like elements promotes the inventive rapid delivery of the substance as well as its penetration into the tissue and is therefore advantageous, particularly in combination.

In a further preferred embodiment of the invention, the substance is a taxane, a statin or a mTOR inhibitor or contains it as a mixture with other substances. It has been shown that these substances are suitable for the use of the medical device in accordance with the invention, in particular with respect to the delivery rate and the action for a genuinely achievable dose.

As an alternative or in addition, a substance is paclitaxel. Paclitaxel has good restenosis-inhibiting properties and has good compatibility.

This is also the case with substances of the limus group, in particular such as sirolimus, everolimus, zotarolimus, biolimus and temsirolimus, and so preferably again, the substance is selected from this group or is a mixture of such substances. Action and compatibility can be enhanced by a suitable combination with further substances, in particular additional substances, wherein the positive action surprisingly exceeds the sum of the individual effects. In this regard, preferably, the medical device in accordance with the invention contains at least one further substance which is suitable for promoting the inhibition of arteriosclerosis and/or the regression of arteriosclerotic plaque and of extending the duration of the action.

Statins, preferably cerivastatin, atorvastatin and/or fluvastatin, and/or antimicrobially acting and/or blood clotting-inhibiting and/or thrombolysis-promoting substances are particularly preferred in this regard.

Particularly preferably, the dose of the substance or substance mixture is >10 $\mu g/mm^2$ of surface area; in particular, a dose in the range from 10 $\mu g/mm^2$ to 50 $\mu g/mm^2$ is preferred. The invention will now be described in more detail with the aid of examples, inter alia. In this regard, the examples are not in any way limiting in effect, nor do the combinations of features which are disclosed limit the scope of the invention.

In a further aspect, the invention concerns a method for coating stents and medical devices of a related form, wherein a coating solution is applied to a surface to be coated at a low temperature, preferably in the range from approximately 0° C. to minus 20° C.

In a preferred embodiment of the method, the coating solution is applied to the surface with the aid of a volumetric measuring device, preferably a syringe, microsyringe or semi-automatically or fully automatically operated piston syringe. This procedure is associated with a comparatively low outlay in respect of equipment and expertise and leads to surprisingly homogeneous results, even with irregular surfaces such as those encountered, for example, with the spike stents described above.

DETAILED DESCRIPTION OF THE PREFERRED EMBODIMENT

Medical Devices for the Coating

Figure 1A:
FIG. 1A is an illustration of a length of an uncoated stent.

Any medical device with a coating which can be coated with rapid-eluting medicinal products in a medically acceptable manner and which is introduced into the body for a short term or permanently is suitable. Metals, synthetic materials or natural products and combinations of products of this type such as stent grafts are suitable as the material. The materials may be plastically or elastically deformable and have shape memory. The surfaces may be smooth, for example polished, or porous or structured or be covered with additional materials.

Medical products which come into contact with the tissue or lumen to be treated for only a short period, i.e. for seconds to a few hours, are preferred. This encompasses medical devices which are removed shortly after use or for which their position in the body is changed during implantation. Examples are self-expandable or balloon-expandable stents the struts of which are displaced during or shortly after implantation against the vessel wall, for example by expansion/post-dilation. By delivering the substance during this process, sections of the vessel wall are supplied with substance which later have no direct contact with the coated stent struts. Coating of a stent of this type is described in Example 15.

A further advantage of the immediate medicinal product delivery is that, shortly after first contact with the tissue, the known compatible struts of the stent contain no polymers or other components of the coating which delay the delivery of the medicinal product and could compromise the compatibility of the stent material. The coatings disclosed here with a particularly high medicinal product dose/mm$^2$ of the surface area of the medical device are particularly advantageous for the very thin-walled and short stents (tacks, which are stents used for spot stenting) which are used only in spots in sections of vessels where balloons alone cannot be sufficiently expanded. These segments of vessel which are difficult to expand mechanically in particular require additional treatment with a drug which inhibits restenosis.

Particularly preferred medical devices are stents which will be mentioned below by way of an example of other medical devices.

Medicinal Products, Substances

In principle, any medicinal products or otherwise pharmacologically effective substances and substance mixtures are suitable. Preferred substances are substances which are slowly released from stents for inhibiting excessive tissue proliferation (for example antineoplastic substances such as paclitaxel and other taxanes as well as sirolimus, everolimus, zotarolimus and other mTOR inhibitors), substances for improving healing, for the inhibition of inflammation, substances which inhibit the advance of processes leading to arteriosclerosis and arteriosclerosis itself, or which promote the regression of arteriosclerotic plaque, such as statins, for example (cerivastatin, atorvastatin, fluvastatin), and substances with an antimicrobial action, or substances for affecting blood clotting, such as heparin and heparin fragments and thrombolytics such as urokinase, streptokinase or recombinant tissue plasmin activators.

Dose

The medical devices and methods in accordance with the invention are used for the targeted therapy of spatially narrow, limited diseased regions of the body. By means of the type of administration, locally high concentrations of substance are obtained despite the small quantities of medicinal product, while the load with respect to the body as a whole remains very low.

The medicinal products are applied to medical devices or are contained in medical devices. When the medical devices make contact with tissue, they are delivered into the body. The dose is with respect to the surface area of the medical device which comes into intimate contact with surfaces within the body, for example arterial walls. This dose on the surface of the medical device in the state of contact with the target tissue is >5 μg of substance or substance mixture/mm$^2$ after sterilization of the medical device, preferably >10 μg/mm$^2$ and most preferably >15 μg/mm$^2$. in the case of stents, these limits also apply to the abluminal faces of the stent struts.

Liquid Preparations for the Coating

Stents and other medical devices are coated with paclitaxel (representing a taxane) and/or rapamycin (mTOR inhibitor, macrolide) and/or with other substances, preferably those mentioned above, wherein the medicinal products are partially or completely dissolved or even suspended in an organic solvent which is immiscible or miscible with water or even which contains water. Preferred solvent mixtures contain ≥10% by volume of water, more preferably ≥15% by volume of water, most preferably ≥20% by volume of water. Preferred concentrations are 10-100 mg of substance or substance mixture in one mL of solution. Preferred organic solvents which are miscible with water are methanol, ethanol, isopropanol, acetone, tetrahydrofuran, dioxane, dimethylsulphoxide. These could contain additional solvents which are immiscible with water or which only take up a little water, examples of which are ether, acetic acid ethyl ester, hexane, cyclohexane, heptane, xylene or other related solvents, or even halogen-containing solvents such as chloroform, dichloromethane or trifluoroethanol.

Application of Medicinal Product to the Medical Device

The stents or other medical devices may be coated by dipping into the substance solutions. The problem in this regard is that only very little solvent and medicinal product adheres to smooth surfaces. The applied dose of medicinal product was substantially higher at low temperatures, for example at approximately 0° C. to minus 20° C. (Example 1) and/or by repeated dipping and drying (see Example 1, Table 2). Increasing the quantity of the adhering material is surprising, because the substance is soluble in the dipping solution. Overall, more substance was applied than for a clinically effective balloon of the same size (4.0×60 mm) at the usual dose of 3 μg/mm$^2$ (2261 μg) and at a substantially higher density of the medicinal product (μg/mm$^2$) on the surface of the medical device (Table 3, right hand column). The coating solution may be sprayed onto the surface. By directed spraying or by means of suitable protective measures, in the case of stents, coating of the post-implantation lumen side (the side directed towards the blood flow) surfaces of the stent can be avoided.

Despite the very delicate form of the stent (see FIGS. 1-6), a defined volume of a coating solution was successfully applied onto the stent surface by means of a microsyringe.

After coating with a liquid preparation, the medical devices are dried.

Preparation of Coated Stents and Comparable Medical Devices for Introduction into Arteries or Other Ducts or Tissues Stents and comparable medical devices (for example balloon catheters) have to be reduced to as small a diameter as possible for introduction into the body. To this end, for example, the diameters of self-expandable stents are compressed and pushed or pulled into narrow tubes. Transfer of the product from the expanded state into an application catheter is facilitated by using a funnel-shaped introduction aid.

Balloons which have been coated in the expanded, inflated state are folded after coating or, insofar as they were folded before coating, they are re-folded, for example by applying a vacuum, and stored in a removable protective sheath. Deformation of the coated structure and rubbing together of the structures both at the tube entrance and in the lumen of the tube cause a loss of coating and/or of medicinal product.

The products for use in patients are sterile. They are preferably sterilized using ethylene oxide; other methods are possible, such as production and packaging under sterile conditions or heat or radiation sterilization.

Application

The coated medical devices are brought to the place of use in the body in as minimally invasive a manner as possible and deployed or inflated there. Shortly after elution of a therapeutically or prophylactically effective dose of a substance, they are removed, their position is changed completely or in part, or they are left implanted. The desired effect is also obtained when the implant is in contact with the tissue which is to be treated therapeutically or tissue in its near vicinity for only a short time.

Example 1

Coating of Stents with Immediate Substantially Complete Delivery of Medicinal Product Upon Implantation Coating solutions: tetrahydrofuran/water 60/40 V/V, 20 mg paclitaxel/mL or ethanol/tetrahydrofuran/water 60/20/20 V/V/V, 20 mg paclitaxel/mL.

$4.0 \times 60$ mm stents having protruding elements for application of the medicinal product were coated (cf. ReFlow US 2017/0196717 or paras 1-3); total surface area of a stent: $188.5$ mm$^2$, by briefly being dipped into the coating solution 8 times. For each layer, the stents were dipped in the solution for 1 sec and then dried for 20 sec in a stream of air at 50° C.

TABLE 2

Paclitaxel onto the coated stents, THF = tetrahydrofuran

| Coating solution | THF/water 60:40 (V/V) | Ethanol/THF/water 60:20:20 (V/V/V) |
|---|---|---|
| Temperature | Room temperature | −20° C. |
| Stent 1 | 193 µg | 860 µg |
| Stent 2 | 171 µg | 886 µg |
| Mean | 182 µg | 873 µg |

Example 2

Coating of Stents with Immediate Substantially Complete Delivery of Medicinal Product Upon Implantation Coating solution: ethanol/acetone/water 40/40/20 V/V/V, 30 mg paclitaxel/mL.

$4.0 \times 60$ mm stents having protruding elements for application of the medicinal product were coated (cf. ReFlow US 2017/0196717), total surface area of a stent: $188.5$ mm$^2$, by briefly being dipped into the cooled coating solution (−20° C.) 10 times. For each layer, the stents were dipped in the solution for 1 sec and then dried for 20 sec in a stream of air at 50° C.

10

TABLE 3

Medicinal product content of coated stents, comparison with angioplasty balloons

| Dimensions: 4.0 × 60 mm | Sample | Surface area mm$^2$ | Paclitaxel on the stent [µg] | [µg/mm$^2$] |
|---|---|---|---|---|
| Stents, 10 × dip-coated | RF-3V3-1 | 188.5 | 2782 | 14.8 |
| | 1 RF-3V3-3 | 188.5 | 3336 | 17.7 |
| Coated angioplasty balloon for comparison | — | 810 | 2850 | 3.5 |

The balloon (clinically tested, effective product) was coated with 3.5 µg paclitaxel/mm$^2$, in total approximately 2850 µg of paclitaxel. In Example 2, Table 3, it can be seen that almost the same dose was successfully deposited onto a substantially smaller surface area.

Figure 1B:
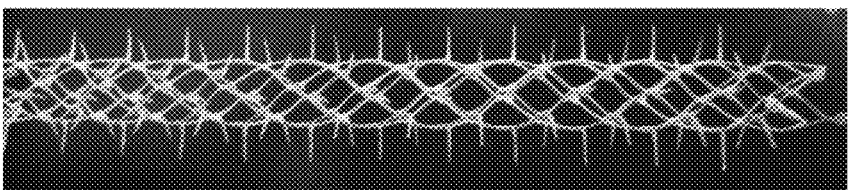
FIG. 1B is a view as in FIG. 1A with a stent that is dip coated.

FIG. 1 in this regard shows, in FIG. 1A, an uncoated stent and in FIG. 1B, a stent which has been dip coated, what is known as a spike stent. Conclusion: despite the small surface area of the stent, it was possible to provide a coat with a dose of similar amplitude on the vessel surface to be treated (defined by the diameter and length of the vessel to be treated) as with a coated balloon catheter.

Example 3

Influence of Repeated Dipping and Drying on the Dose on the Stent

Coating solutions:
(a) ethanol/tetrahydrofuran/water (60/20/20), 20 mg paclitaxel/mL
(b) ethanol/acetone/water (40/40/20 V/V/V), 30 mg paclitaxel/mL Stents as described in Example 1 were coated by brief repeated dipping into cooled coating solutions (−20° C.) coating solutions. For each layer, the stents were dipped in the solution for 1 sec and then dried for 20 sec in a stream of air at 50° C.

TABLE 4

Coating of stents by repeated dipping into solutions of medicinal products, paclitaxel content of stents; influence of repetition of coating on the medicinal product content of the stents

| | Coating solution: ethanol/ tetrahydrofuran/ water (60/20/20), 20 mg paclitaxel/mL | | Coating solution: ethanol/acetone/ water (40/40/20), 30 mg paclitaxel/mL | |
|---|---|---|---|---|
| Coating cycles | Coated quantity of paclitaxel [µg] | Dose [µg/mm$^2$ stent surface area] | Coated quantity of paclitaxel [µg] | Dose [µg/mm$^2$] |
| 2 | 275 | 1.46 | 372 | 1.97 |
| 4 | 588 | 3.12 | 745 | 3.95 |
| 6 | 662 | 3.51 | 1059 | 5.62 |
| 8 | 788 | 4.18 | 1732 | 9.19 |
| 10 | 1104 | 5.86 | 2536 | 13.45 |

$4.0 \times 60$ mm stents having protruding elements for application of the medicinal product were coated (cf. ReFlow US 2017/0196717) by brief repeated dipping into cooled coating solutions. "Coating cycle" means that the stents were dipped into the solution for 1 second and then dried for 20 sec in a stream of air at 50° C.

The entire surface area of the stent was 188.5 mm$^2$ and was therefore substantially smaller than the surface area of the correspondingly dimensioned balloon (810 mm$^2$).

Example 4

Loss of Medicinal Product During the Introduction of Coated Stents into the Catheter Provided for Administration Through a Tapered Channel 4.0×60 mm stents having protruding elements for application of the medicinal product were coated (cf. ReFlow US 2017/0196717) by brief repeated dipping into cooled coating solutions. "Coating cycle" means that the stents were dipped into the solution cooled to −20° C. for 1 second and then dried for 20 sec in a stream of air at 50° C. Eight coating cycles were carried out.

Coating solution: ethanol/acetone/water, wherein the proportions of ethanol and acetone were respectively 40% by volume and the proportion of water was 20% by volume. The paclitaxel concentration in the coating solution was 24 mg/mL.

TABLE 5

| | Paclitaxel on the stents after dip coating eight times |
| --- | --- |
| Sample | Paclitaxel content directly after coating [µg] |
| RF3b2-1 | 1711 |
| RF3b2-4 | 1423 |
| RF3b2-7 | 1547 |
| Mean ± SD | 1560 ± 145 |

The coated stents were compressed to a small diameter by passage through a stainless steel block with tapered holes and then introduced into the lumen of the application catheter; the paclitaxel content of the flattened particles was determined. These particles contained a total (n=6) of only 0.42±0.37% of the medicinal product dose on the stent.

TABLE 6

| | Loss of coating during compression of the stent and introduction into the application catheter | |
| --- | --- | --- |
| Sample name | Paclitaxel loss [µg] | % of paclitaxel dose (Table 5) |
| RF-3b2-2 load | 3.8 | 0.24 |
| RF-3b2-3 load | 13.7 | 0.88 |
| RF-3b2-5 load | 4.0 | 0.26 |
| RF-3b2-6 load | 1.2 | 0.08 |
| RF-3b2-8 load | 14.4 | 0.92 |
| RF-3b2-9 load | 3.0 | 0.19 |
| Mean ± SD | 6.7 ± 5.8 | 0.42 ± 0.37 |

Dip coating: paclitaxel 24 mg/mL ethanol/acetone/water 40/40/20 V/V/V.

Example 5

Coating of Stents with Immediate Substantially Complete Delivery of Medicinal Product Upon Implantation with a Measured Volume of Coating Solution Coating solution (a): ethanol/acetone/water or (b): ethanol/THF/water, wherein the proportion of ethanol was respectively 40% by volume, the proportion of acetone or THF was 40% or 50% by volume and the proportion of water corresponded to 20% or 10% by volume. The paclitaxel concentration in the coating solution was 12.5 mg/mL. Coating was carried out by rotation of the medical device (21 rpm) and using a Hamilton microsyringe with a volume of 75 µL/stent (4.0×60 mm). 4.0×60 mm stents having protruding elements for application of the medicinal product were coated (cf. ReFlow US 2017/0196717), total surface area of a stent=188.5 mm$^2$, by distributing the solution over the irregular surface of the stent.

Using this method also produced an unexpectedly uniform, white coating on the silver-grey metallic stent.

Figure 2:
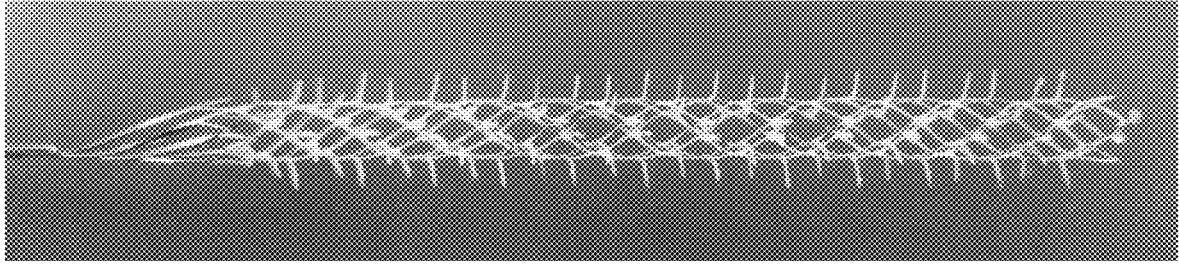
FIGS. 2-6 are views corresponding to those in FIG. 1B and showing alternative forms of stents.

The stent shown in FIG. 2 has a coating. This was applied by means of a RF—3d coating solution (paclitaxel 12.5 mg/mL ethanol/acetone/water 40/50/10 V/V/V, applied by means of a Hamilton syringe.

TABLE 7

| | Paclitaxel on the stents after introduction into the application system (compression of stent, storage in narrow-lumen tube) and subsequent deployment | | | | |
| --- | --- | --- | --- | --- | --- |
| | Paclitaxel in catheter with stent | | | Paclitaxel on deployed stents | |
| Sample | [µg] | Mean ± SD | Sample | [µg] | Mean ± SD |
| RF-sd3c-1 | 1333 | 1259 ± 149 | RF-s4a-1 | 1033 | 1223 ± 118 |
| RF-sd3c-2 | 1128 | | RF-s4a-2 | 1175 | |
| RF-sd3c-3 | 1337 | | RF-s4a-3 | 1237 | |
| RF-sd3d-1 | 1422 | | RF-s4a-1 | 1331 | |
| RF-sd3d-2 | 1075 | | RE-s4a-2 | 1203 | |
| RF-sd3d-3 | No value | | RF-s4a-3 | 1361 | |

Example 6

Coating of Stents with Immediate Substantially Complete Delivery of Medicinal Product Upon Implantation with a Measured Volume of the Coating Solution Coating solution: ethanol/acetone/THF/water, wherein the proportions of ethanol, acetone and THF were respectively 30% by volume and the proportion of water corresponded to 10% by volume. The paclitaxel concentration in the coating solution was 20 mg/mL. Coating was carried out by rotation of the medical device (21 rpm) and using a Hamilton microsyringe with a volume of 75 µL/per stent (4.0×60 mm).

4.0×60 mm stents having protruding elements for application of the medicinal product were coated (cf. ReFlow US 2017/0196717), total surface area of a stent=188.5 mm$^2$, by distributing the solution over the irregular surface of the stent.

Figure 3:
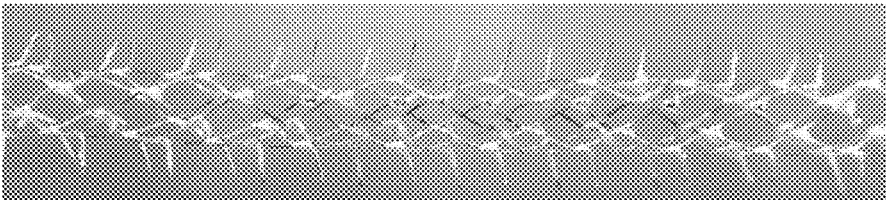

FIG. 3, like FIG. 2, shows a photographic image of a portion of a coated stent. For the coating, a RF-G-20 coating solution (paclitaxel 20 mg/mL, ethanol/acetone/THF/water 30/30/30/10 (V/V)), was also applied with a Hamilton syringe.

TABLE 8

Paclitaxel on the stents directly after coating and loss
upon introduction into the application system

| | Paclitaxel on the stents directly after coating [μg] | | Loss of paclitaxel upon introduction into the application system [μg] | | |
|---|---|---|---|---|---|
| Sample | Measurements | Mean ± SD | Sample | Measurements | Mean ± SD |
| RF-G-20-1 | 1462 | 1420 ± 36 | RF-G-20-2 | 89 | 90 ± 38 |
| RF-G-20-3 | 1401 | | RF-G-20-4 | 53 | |
| RF-G-20-5 | 1397 | | RF-G-20-6 | 128 | |

Example 7

Coating of Stents with Immediate Substantially Complete Delivery of Medicinal Product Upon Implantation with a Measured Volume of the Coating Solution Coating solution: ethanol/acetone/water, wherein the proportions of ethanol and acetone were respectively 40% by volume and the proportion of water corresponded to 20% by volume. The paclitaxel concentration in the coating solution was 20 mg/mL. In addition, iopromide was added in a concentration of 2 mg/mL. Coating was carried out by rotation of the medical device (21 rpm) and using a Hamilton microsyringe with a volume of 75 μL/Stent (4.0×60 mm).

4.0×60 mm stents having protruding elements for application of the medicinal product were coated (cf. ReFlow US 2017/0196717), total surface area of a stent=188.5 mm², by distributing the solution over the irregular surface of the stent.

Figure 4:
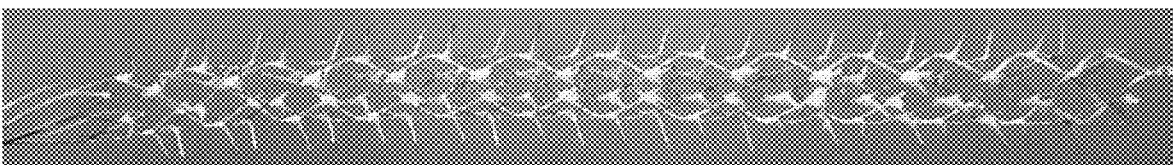

A stent coated in this manner is shown in FIG. 4. The coating solution used was a RF-C-20-UV-2 solution (paclitaxel 20 mg/mL and iopromide (2 mg/mL), ethanol/acetone/water 40/40/20 (V/V)). Application to the stent was again carried out with a Hamilton syringe.

TABLE 9

Paclitaxel on the stents directly after coating and loss upon introduction
into the application system, no increase of loss with iopromide

| | Paclitaxel on the stents directly after coating | | | Loss of paclitaxel upon introduction into the application system | |
|---|---|---|---|---|---|
| Sample | [μg] | Mean ± SD | Sample | [μg] | Mean ± SD |
| RF-C-20-UV-2-1 | 1440 | 1437 ± 25 | RF-C-20-UV-2-2 | 94 | 80 ± 30 |
| RF-C-20-UV-2-3 | 1411 | | RF-C-20-UV-2-4 | 100 | |
| RF-C-20-UV-2-5 | 1460 | | RF-C-20-UV-2-6 | 45 | |

Example 8

Coating of Stents with Immediate Substantially Complete Delivery of Medicinal Product Upon Implantation with a Measured Volume of the Coating Solution Coating solution: ethanol/acetone/water, wherein the proportions of ethanol and acetone were respectively 40% by volume and the proportion of water corresponded to 20% by volume. The paclitaxel concentration in the coating solution was 20 mg/mL. In addition, dexpanthenol was added in a concentration of 2 mg/mL. Coating was carried out by rotation of the medical device (21 rpm) and using a Hamilton microsyringe with a volume of 75 μL/per stent (4.0×60 mm).

4.0×60 mm stents having protruding elements for application of the medicinal product were coated (cf. ReFlow US 2017/0196717), total surface area of a stent=188.5 mm², by distributing the solution over the irregular surface of the stent.

Figure 5:
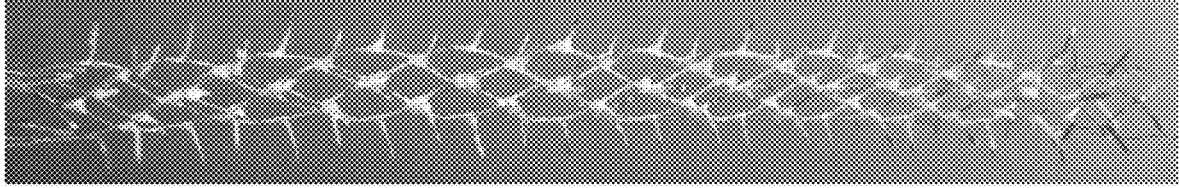

FIG. 5 shows a stent coated with RF-C-20-DP-2 coating solution, see Table 10 (paclitaxel 20 mg/mL and dexpanthenol (2 mg/mL) in ethanol/acetone/water 40/40/20 (V/V)). Here again, application to the stent was carried out with a Hamilton syringe.

TABLE 10

Paclitaxel on the stents directly after coating and loss upon introduction
into the application system, no increase of loss with dexpanthenol

| | Paclitaxel on the stents directly after coating | | | Loss of paclitaxel upon introduction into the application system | |
|---|---|---|---|---|---|
| Sample | [μg] | Mean ± SD | Sample | [μg] | Mean ± SD |
| RF-C-20-DP-2-1 | 1462 | 1460 ± 78 | RF-C-20-DP-2-2 | 64 | 60 ± 11 |
| RF-C-20-DP-2-3 | 1536 | | RF-C-20-DP-2-4 | 68 | |
| RF-C-20-DP-2-5 | 1381 | | RF-C-20-DP-2-6 | 48 | |

Example 9

Coating of Stents with Immediate Substantially Complete Delivery of Medicinal Product Upon Implantation, with a Measured Volume of the Coating Solution Coating solution: ethanol/acetone/water, wherein the proportions of ethanol and acetone were respectively 40% by volume and the proportion of water corresponded to 20% by volume. The paclitaxel concentration in the coating solution was 20 mg/mL. In addition, urea was added in a concentration of 2 mg/mL. Coating was carried out by rotation of the medical device (21 rpm) and using a Hamilton microsyringe with a volume of 75 μL/per stent (4.0×60 mm).

4.0×60 mm stents having protruding elements for application of the medicinal product were coated (cf. ReFlow US 2017/0196717), total surface area of a stent=188.5 mm², by distributing the solution over the irregular surface of the stent.

Figure 6:
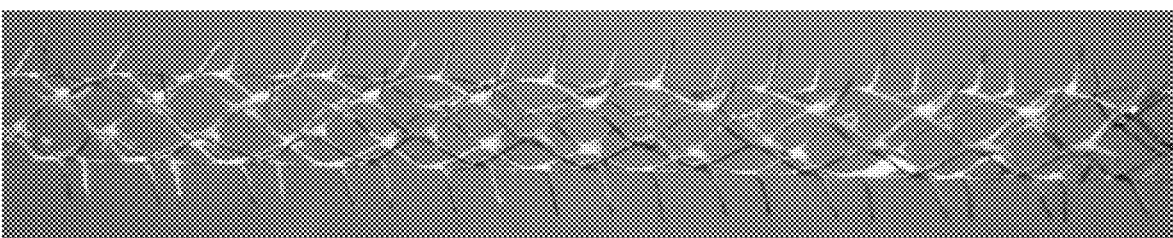

The stent coating in the stent shown in FIG. 6 was obtained by means of a RF-C-20-UR-2 coating solution (paclitaxel 20 mg/mL and urea (2 mg/mL), ethanol/acetone/water 40/40/20 (V/V), applied by means of a Hamilton syringe.

TABLE 11

Paclitaxel on the stents directly after coating and loss upon introduction into the application system, no increase of loss with urea

| | Paclitaxel on the stents directly after coating | | | Loss of paclitaxel upon introduction into the application system | |
|---|---|---|---|---|---|
| Sample | [μg] | Mean ± SD | Sample | [μg] | Mean ± SD |
| RF-C-20-UR-2-1 | 1392 | 1432 ± 37 | RF-C-20-UR-2-2 | 47 | 66 ± 38 |
| RF-C-20-UR-2-3 | 1438 | | RF-C-20-UR-2-4 | 109 | |
| RF-C-20-UR-2-5 | 1466 | | RF-C-20-UR-2-6 | 41 | |

Example 10

Coating of Stents and Subsequent Fitting onto Uncoated Balloon Catheters

Stents having protruding elements for application of the medicinal product (cf. ReFlow US 2017/0196717) were provided with a coating which upon implantation guaranteed an immediate, substantially complete delivery of medicinal product. The coating solution contained 20 mg/mL paclitaxel or 20 mg/mL paclitaxel and 2 mg/mL dexpanthenol. The solvent mixture used was ethanol/acetone/water, wherein the proportions of ethanol and acetone were respectively 40% by volume and the proportion of water corresponded to 20% by volume. Coating was carried out with rotation (21 rpm) using a Hamilton microsyringe with a volume of 75 μL/stent.

Balloon catheters with balloons of an appropriate size (balloon diameter=stent diameter, balloon length=stent length) were introduced into the application catheter for the stent from the proximal end, so that distally, the balloon protruded completely out of the application catheter. After coating, the stents were pushed over a folded balloon of the balloon catheter and subsequently adhered to the shaft of the balloon catheter, so that the balloon was located in the lumen of the coated stent. By pulling the balloon shaft lying in the application catheter through a metal block with tapered holes, the balloon and stent were compressed to the diameter of the application catheter and introduced into the latter.

Example 11

Coating of (a) Balloons of Balloon Catheters and (b) Stents with Subsequent Fitting of Coated Stent onto the Coated Balloon Catheter Folded balloons (4.0×80 mm) of balloon catheters were inflated and coated under rotation (21 rpm). The coating solution contained 20 mg/mL paclitaxel or 20 mg/mL paclitaxel and 2 mg/mL dexpanthenol. The solvent mixture used was ethanol/acetone/water, wherein the proportions of ethanol and acetone were respectively 40% by volume and the proportion of water corresponded to 20% by volume. The coating was carried out with a volume of 75 μL using a Hamilton syringe. The coated balloons were deflated and re-folded under vacuum by pushing on a PTFE tube.

Balloon catheters with coated folded balloons were introduced into the application catheter for the stent from the proximal end, so that distally, the balloon protruded completely out of the application catheter.

Stents having protruding elements for application of the medicinal product (cf. ReFlow US 2017/0196717) were provided with a coating which, upon implantation, guaranteed an immediate, substantially complete delivery of medicinal product. The coating solution contained 20 mg/mL paclitaxel or 20 mg/mL paclitaxel and 2 mg/mL dexpanthenol. The solvent mixture used was ethanol/acetone/water, wherein the proportions of ethanol and acetone were respectively 40% by volume and the proportion of water corresponded to 20% by volume. Coating was carried out with rotation (21 rpm) using a Hamilton microsyringe with a volume of 75 μL/stent.

After coating, the stents were pushed the re-folded balloon of the balloon catheter described above and then adhered to the shaft of the balloon catheter so that the balloon was located in the lumen of the coated stent.

By pulling the balloon shaft lying in the application catheter through a metal block with tapered holes, the balloon and stent were compressed to the diameter of the application catheter and introduced into the latter.

Example 12

Coating of Stents with a Balloon of a Balloon Catheter in the Stent Lumen

The initially uncoated stents with the similarly uncoated balloons of the balloon catheter were in an application catheter. The distal end of the balloon catheter protruded from the application catheter with the balloon and stent. The stents with the protruding elements for medicinal products application, which were fastened to the shaft of a balloon catheter and for which the balloon was located in the lumen of the stent, were provided with a coating which guaranteed an immediate substantially complete delivery of medicinal product upon implantation.

The coating solution contained 20 mg/mL paclitaxel or 20 mg/mL paclitaxel and 2 mg/mL dexpanthenol. The solvent mixture used was ethanol/acetone/water, wherein the proportions of ethanol and acetone were respectively 40% by volume and the proportion of water corresponded to 20% by volume. Coating was carried out with rotation (21 rpm) with a volume of 75 μL/per stent (4.0×60 mm) using a Hamilton microsyringe.

After drying, the balloon and stent were compressed to the diameter of the application catheter by pulling the balloon shaft lying in the application catheter through a metal block with tapered holes and introduced into the application catheter.

Example 13

Coating of Balloons of Balloon Catheters and Fitting in the Lumen of Uncoated Stents Balloon catheters with folded balloons of an appropriate size (balloon diameter=stent diameter, balloon length=stent length+20 mm) were introduced into the application catheter for the stent from the proximal end, so that distally, the balloon protruded completely out of the application catheter.

The balloons (4.0×80 mm) were inflated and coated under rotation (21 rpm). The coating solution contained 20 mg/mL paclitaxel or 20 mg/mL paclitaxel and 2 mg/mL dexpanthenol. The solvent mixture used was ethanol/acetone/water, wherein the proportions of ethanol and acetone were respectively 40% by volume and the proportion of water corresponded to 20% by volume. Coating was carried out with a volume of 75 μL using a Hamilton microsyringe. The coated balloons were deflated after drying and re-folded under vacuum by pushing on a PTFE tube. The PTFE tubes were later removed.

Uncoated stents having protruding elements for application of the medicinal product (cf. ReFlow US 2017/0196717) were pushed over the coated balloons and adhered to the shaft of the balloon catheter in a manner such that the balloon was located in the lumen of the uncoated stent.

The balloon and stent were compressed to the diameter of the application catheter by pulling the balloon shaft in the application catheter through a metal block with tapered holes and introduced into the application catheter.

Example 14

Application Test of Stents with Immediate Substantially Complete Delivery of Medicinal Product Upon Implantation into Pigs Following sterilization, stents from Examples 4, 5a, 7 and 8 were introduced into the iliaca interna, arteria femoralis and arteria profunda femoris of pigs (approx. 30 kg body weight) and deployed from the application catheter, then completely expanded for 2 min with an uncoated balloon catheter and then completely removed through a special retrieval mechanism without injuring the animal. Approximately 15 min after removal of the stent, in the case of using the stent of Example 4, 4.2±4.0% of the paclitaxel dose, of Example 5a, 5.1±2.4% of the dose, of Example 7, 4.0±0.6% of the dose and of Example 8, 9.9±7.0% of the dose was found in the arterial wall. These values were similar to the values measured after using clinically proven coated balloons (Scheller B, Speck U, Abramjuk C, Bermhardt U, Böhm M, Nickenig G. Paclitaxel balloon coating—a novel method for prevention and therapy of restenosis. Circulation 2004; 110: 810-814; Kelsch B, Scheller B, Biedermann M, Clever Y P, Schaiffner S; Mahnkopf D; Speck U, Cremers B. Dose-response to paclitaxel-coated balloon catheters in the porcine coronary overstretch and stent implantation model. Invest Radiol 2011; 46:255-263). On average, 20% of the dose remained on the stents.

Example 15

Coating of Self-Expanding Nitinol Stents for Peripheral Arteries (VascuFlex®) Peripheral Stent, B. Braun Vascular Systems) 8×60 mm, Approx. 700 mm=Surface Area, Coated Using a Hamilton Microsyringe, Coating Solution: Ethanol/Acetone/Water 40140/20 V/V/V, 30 mg Paclitaxel/mL

TABLE 12

Paclitaxel on the stents directly after coating; loss upon introduction into the application system, reproducible coating of stents with a nitinol main body with resveratrol-containing coating solution.

| Formulation | N | O | P | Q |
|---|---|---|---|---|
| Composition | 25 mg/mL PTX, | 50 mg/mL PTX, | 50 mg/mL PTX, | 25 mg/mL PTX, |

TABLE 12-continued

Paclitaxel on the stents directly after coating; loss upon introduction into the application system, reproducible coating of stents with a nitinol main body with resveratrol-containing coating solution.

| Formulation | N | O | P | Q |
|---|---|---|---|---|
| | 7.5 mg/mL resveratrol acetone/ THF/$H_2O$ (50/36/14) | 15 mg/mL resveratrol THF/$H_2O$ (80/20) | 15 mg/mL resveratrol acetone/ THF/$H_2O$ (38/32/30) | 7.5 mg/mL resveratrol acetone/ THF/$H_2O$ (46/96/15) |
| Coating volume [μL] | 84 | 42 | 42 | 84 |
| Content after coating, in μg/Stent | 1919 ± 53 | 1966 ± 26 | 1677 ± 105 | 2048 ± 31 |

The invention claimed is:

1. An implantable medical device, coated with a releasable substance or substance mixture, for arteriosclerosis-conditioned vascular stenosis, comprising a main body with a substance and/or a substance mixture applied to a surface of the main body, and wherein the dose of the substance or of the substance mixture is >10 μg/mm$^2$ with respect to the coated surface area, wherein the implantable medical device allows at least 60% of the releasable substance or substance mixture originally disposed on the surface of the main body to be delivered into a surrounding tissue within no more than 20 minutes after the implantable medical device is implanted within a human body, and wherein the implantable medical device is not a balloon catheter.

2. The implantable medical device as claimed in claim 1, wherein the main body consists of a metal, a synthetic material, a natural product or a combination of these materials, and is deformable.

3. The implantable medical device as claimed in claim 1, wherein the substance is a taxane, a statin or an mTOR inhibitor or comprises a taxane, a statin or an mTOR inhibitor as a mixture with other substances.

4. The implantable medical device as claimed in claim 1, wherein the medical device comprises a lumen, wherein the lumen comprises a balloon configured for dilation and having a coating comprising a substance for dilation.

5. The implantable medical device as claimed in claim 1, wherein the medical device is in the form of a stent and wherein the medical device comprises a lumen, wherein the lumen comprises a balloon configured for post-dilation and having a coating comprising a substance for post-dilation.

6. The implantable medical device as claimed in claim 1, which comprises at least one further substance which inhibits arteriosclerosis and/or which promotes the regression of arteriosclerotic plaque, and/or which inhibits blood clotting and/or which promotes thrombolysis.

7. The implantable medical device as claimed in claim 1, wherein the substance is or comprises paclitaxel.

8. The implantable medical device as claimed in claim 1, wherein the substance is selected from sirolimus, everolimus, zotarolimus, biolimus and temsirolimus or comprises one of sirolimus, everolimus, zotarolimus, biolimus and temsirolimus, and/or comprises a substance mixture with one of sirolimus, everolimus, zotarolimus, biolimus and temsirolimus.

9. The implantable medical device as claimed in claim 1, wherein the implantable medical device is or comprises a stent.

10. The implantable medical device as claimed in claim 1, wherein the main body consists of steel or cobalt-chrome, and is deformable.

11. The implantable medical device as claimed in claim 6, wherein the at least one further substance comprises statins and/or has an antimicrobial action.

12. The implantable medical device as claimed in claim 1, wherein the main body comprises nitinol.

\* \* \* \* \*